United States Patent [19]

Vladuchick

[11] 4,067,879

[45] Jan. 10, 1978

[54] 1,4-DITHIINO[2,3-C; 6,5-C']DIISOTHIAZOLE AND RELATED COMPOUNDS

[75] Inventor: Susan Anne Vladuchick, Newark, Del.

[73] Assignee: E. I. Du Pont de Nemours and Company, Wilmington, Del.

[21] Appl. No.: 719,833

[22] Filed: Sept. 7, 1976

Related U.S. Application Data

[63] Continuation-in-part of Ser. No. 625,132, Oct. 23, 1975, abandoned.

[51] Int. Cl.$^2$ .............................................. C07D 513/14
[52] U.S. Cl. .......................... 260/302 F; 252/301.28; 260/78 UA; 260/268 TR
[58] Field of Search ..................................... 260/302 F

[56] References Cited

U.S. PATENT DOCUMENTS

| 3,101,344 | 8/1963 | Vest | 260/302 F |
| 3,101,365 | 8/1963 | Vest | 260/302 F |

Primary Examiner—R. Gallagher

[57] ABSTRACT

The compound 3,7-dicyano-1,4-dithiino[2,3-c; 6,5-c']diisothiazole is prepared by reacting either tetracyano-1,4-dithiin or 4,5-dicyano-1,3-dithiolen-2-one with sulfur in 1,2-dimethoxyethane at a temperature of 50°–280° C in the presence of a basic catalyst. The diisothiazole can be converted to derivatives with various utilities, e.g., as fluorescent brighteners.

10 Claims, No Drawings

1,4-DITHIINO[2,3-c; 6,5-c']DIISOTHIAZOLE AND RELATED COMPOUNDS

CROSS-REFERENCE TO RELATED APPLICATION

This application is a continuation-in-part of application Ser. No. 625,132 filed Oct. 23, 1975, now abandoned.

BACKGROUND OF THE INVENTION

1. Field of the Invention

This invention relates to diisothiazoles and more particularly to a tricyclic heterocyclic ring system, 1,4-dithiino[2,3-c; 6,5-c']diisothiazole and ring-substituted derivatives thereof.

2. Relation to the Prior Art

The applicant is not aware of any art which discloses the tricyclic isothiazole ring systems of this invention. U.S. Pat. No. 3,101,344 issued Aug. 20, 1963, to R. D. Vest discloses bicyclic p-dithiino[c]isothiazole-3,5,6-tricarbonitrile, thus,

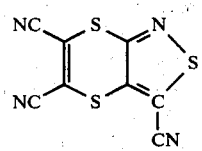

as a side product in the preparation of tetracyano-1,4-dithiin. Simmons et al., J. Am. Chem. Soc. 84, 4746 (1962), disclose the preparation of this tricarbonitrile by reaction of tetracyano-1,4-dithiin with sulfur, iodine and sodium iodide at 25° C.

SUMMARY OF THE INVENTION

The diisothiazoles of the invention have the structure:

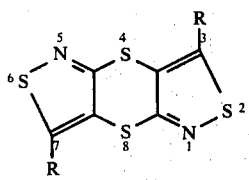

wherein
both R's are the same and are -H, -CN, -COCl, -CO$_2$R$^1$, -CONR$^2$R$^3$ or -CO$_2$-(alkyl)$_4$N+,
R$^1$ is -H, alkyl of 1-5 carbon atoms, phenyl or benzyl;
R$^2$ and R$^3$ are each selected from the group consisting of -H, alkyl of 1-5 carbon atoms, phenyl and phenyl substituted with alkyl, alkoxy, nitro, halo, or dialkylamino, in which the alkyl is from 1-5 carbon atoms.

This invention also comprises a method of making the above compounds which comprises the essential step of contacting and reacting tetracyano-1,4-dithiin:

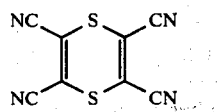

4,5-dicyano-1,3-dithiolen-2-one:

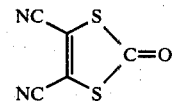

with sulfur in 1,2-dimethoxyethane (glyme) solvent at a temperature in the range of 50°–280° C, preferably 75°–85° C, in the presence of a basic catalyst. The cyano groups can be converted to acid, amide or ester groupings, if desired, by conventional methods.

DETAILED DESCRIPTION OF THE INVENTION

The 3,7-dicyano-1,4-dithiino[2,3-c; 6,5-c']diisothiazole of formula I where R=CN is prepared by reaction of tetracyano-1,4-dithiin or 4,5-dicyano-1,3-dithiolen-2-one with sulfur in the presence of a basic catalyst in 1,2-dimethoxyethane solvent according to the following reaction:

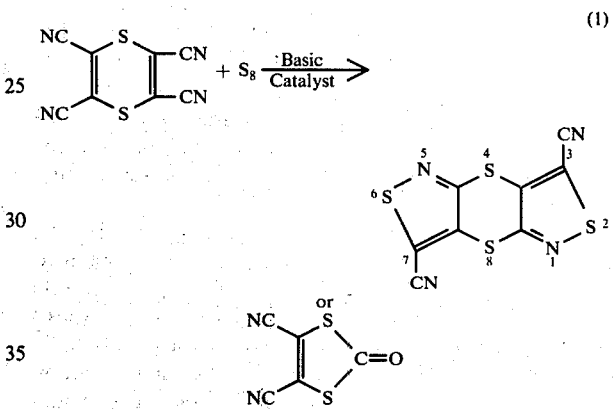

(1)

Although the reactants can be mixed together in any order, it is preferred to premix the catalyst and sulfur with the solvent, heat briefly to reflux temperature to dissolve the reactants, and add the tetracyano-1,4-dithiin or 4,5-dicyano-1,3-dithiolen-2-one last.

Tetracyano-1,4-dithiin is prepared as described in the aforesaid U.S. Pat. No. 3,101,344 and 4,5-dicyano-1,3-dithiolen-2-one is prepared as described in U.S. Pat. No. 3,140,295, issued July 7, 1964, to Carl George Krespan.

The reaction temperature is not particularly critical so long as a minimum reaction temperature of at least about 50° C is employed. Thus, at reaction temperatures significantly below about 50° C, e.g. room temperature, the reaction does not proceed to give the desired 3,7-dicyano-1,4-dithiino[2,3-c; 6,5-c']diisothiazole. Higher reaction temperatures may be employed, e.g. up to about 280° C. It is preferred to operate at temperatures of about 75°–85° C since the reaction is conveniently carried out near the reflux temperature of the solvent (83°–84° C) at about atmospheric pressure.

The ratio of reactants, i.e., sulfur to tetracyano-1,4-dithiin or 4,5-dicyano-1,3-dithiolen-2-one, is not particularly critical. However, since an equivalent ratio of at least 2:1 sulfur:tetracyano-1,4-dithiin or 4,5-dicyano-1,3-dithiolen-2-one is required for complete reaction of the dithiin or dithiolene, it is preferred that the equivalent ratio of these reactants be at least 2:1. It is further preferred to use a higher equivalent ratio, i.e. up to about 5:1 since the reaction proceeds more rapidly in the presence of excess sulfur. When excess sulfur is used and/or reaction time is shortened during the reaction with dithiin, a side product is formed together with 3,7-dicyano-1,4-dithiino[2,3-c; 6,5-c']diisothiazole. Since the side product is more soluble in the reaction medium it is readily separated from the major product.

Illustrative, suitable basic catalysts for the reaction are tertiary aliphatic amines, polysulfides, alkali metal iodides and alkali metal sulfides. Specific catalysts within this group are sodium iodide, potassium iodide, lithium iodide, sodium polysulfide, potassium polysulfide, triethylamine, tri-n-propylamine, diisopropylethylamine, diisopropylmethylamine, tri-n-butylamine, N,N-dimethylcyclohexylamine, alkali metal and tetraalkylammonium salts of bis(2-mercapto-1,2-dicyanovinyl)sulfide, e.g., the sodium, potassium, tetramethylammonium, tetraethylammonium, tetrapropylammonium and tetra-n-butylammonium salts. Preferred catalysts are alkali metal iodides, particularly sodium iodide, because of the high yields of product obtained, and tertiary aliphatic amines because of their high catalytic efficiency in lowering reaction times. It is preferred that the molar ratio of catalyst to tetracyano-1,4-dithiin or 4,5-dicyano-1,3-dithiolen-2-one be about 1:20 to 1:5.

Reaction time is not critical and times of about 1-24 hours are conveniently employed depending upon the catalyst selected. Examples 1-5 and 21 illustrate these preparations of structure I (R=CN).

The compounds of the invention where R=-H, -COCl, -CO$_2$R$^1$, and -CONR$^2$R$^3$ are readily obtained from 3,7-dicyano-1,4-dithiino[2,3-c; 6,5-c']diisothiazole (R = CN in formula I) by applying known procedures for conversion of nitrile groups to amides, carboxylic acids, esters and acid chlorides. For example, reaction of the aforesaid compound with sulfuric acid at elevated temperatures causes hydrolytic decarboxylation and a product of formula I where R = H is obtained as shown in Examples 6 and 7 below.

Alternatively, basic hydrolysis of the aforesaid compound with aqueous potassium hydroxide followed by acidification gives the corresponding dicarboxylic acid (formula I, R=-CO$_2$H) as shown in Example 8. Hydrolysis with concentrated hydrochloric acid (Example 9) also gives the dicarboxylic acid.

The diacid chloride (formula I, R = -COCl) is obtained from the dicarboxylic acid by reaction with conventional reagents such as thionyl chloride or PCl$_3$ (Example 10). The diacid chloride in turn can be used for the preparation of amides by reaction with a suitable amine (Examples 11, 15-20), or for the preparation of esters by reaction with an alcohol (Examples 12-14).

Alternatively, esters (formula I, R=-CO$_2$R$^1$) can be prepared directly from the dicarboxylic acid by reaction with an alcohol in the presence of an acid catalyst. Also, salts (formula I, R = -CO$_2^-$ (alkyl)$_4$N+) can be prepared from the dicarboxylic acid by reaction with a tetra-alkyl ammonium hydroxide (Example 22).

EMBODIMENTS OF THE INVENTION

The following are illustrative examples of the invention in which all parts and percentages are by weight and all temperatures in degrees Centigrade unless otherwise stated. Elemental analysis values written with a bar are averages of two or more determinations.

EXAMPLE 1

3,7-Dicyano-1,4-dithiino[2,3-c; 6,5-c']diisothiazole (Formula I, R = -CN)

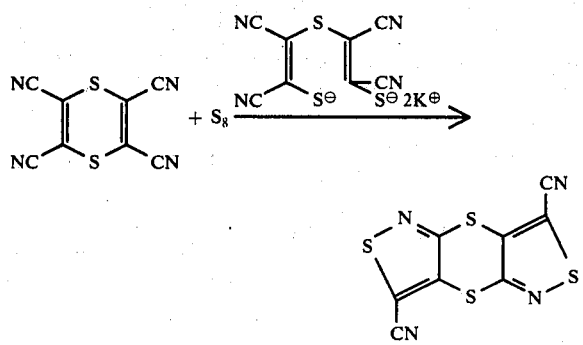

Tetracyano-1,4-dithiin (4.32 g, 20 meq) was added to a stirred solution of sulfur (2.69 g. 84 meq) and the dipotassium salt of bis(2-mercapto-1,2-dicyanovinyl)sulfide catalyst (0.6 g, 2 meq) in 200 ml of 1,2-dimethoxyethane. The yellow-green solution quickly turned dark orange, and the reaction mixture was heated under reflux (83°-84° C) overnight. The solution was cooled and the solvent removed at reduced pressure. The residue was extracted with water and filtered to leave an 87% yield of crude solid product. This crude product was sublimed at 235° C (0.1 mm, oil pump) and it was recrystallized twice from toluene to give pure 3,7-dicyano-1,4-dithiino[2,3-c; 6,5-c']diisothiazole as a pale yellow solid, mp 286°-289° C.

Anal. Calcd. for C$_8$N$_4$S$_4$: C, 34.3; N, 20.0; S, 45.7. Found: C, 34.6; N, 20.0; S, 45.4.

The following spectral and analytical data confirm the structure of formula I:

A. Infrared maxima (IR(KBr)): 4.50 (s, CN), 6.78 (s), 7.48, 7.58, 7.78(s), 8,68, 10.43(s), 11.85(s), 12.30(s), 14.58, 14.98 microns($\mu$).

B. Dipole moment measured at 25° C in dioxane, $\mu$ = 3.82D; 3.59D.

Additional analytical data were obtained on another sample of the product.

C. Ultraviolet maxima UV(CH$_3$CH): $\lambda$ max 338 nm ($\epsilon$ 10,900), 278 (14,950), 218 (25,000).

D. Carbon — 13 nuclear magnetic resonance spectrum ($^{13}$C-nmr) was run in dimethyl sulfoxide -d$_6$(DMSO-d$_6$) at 100° C. Chromium acetylacetonate (0.01 g.) was added to lock signals. The analysis showed four nonequivalent carbon atoms at 153.2, 133.0, 127.2 and 108.3 (CN) ppm from tetramethylsilane reference.

E. High resolution mass spectral analysis showed a measured m/e of 279.8988 in agreement with the molecular formula C$_8$N$_4$S$_4$(Calcd. for C$_8$N$_4$S$_4$: m/e 279.9006).

F. The crystal and molecular structures of 3,7-dicyano-1,4-dithiino[2,3-c; 6,5-c']diisothiazole were determined from three-dimensional X-ray data collected by counter methods such as on a Picker diffractometer. The molecular conformation is unambiguously established as trans as shown in formula I. The molecular point symmetry is C$_2$(2) with the twofold axis normal to the 1,4-sulfur atoms. The molecule is folded along the 1,4-S--S direction and planar to within 0.04 A on both sides of the fold. The angle of fold is 144.9° as measured by the angle between the two 5-membered isothiazole rings. The folded molecules are stacked along the $b$ axis with 3.808A between sulfur atoms on adjacent molecules; the perpendicular distance between isothiazole rings is 3.614A.

Crystals are monoclinic, space group C2/c, with $a = 12.836 \pm 0.006$, $b = 3.808 \pm 0.002$, $c = 21.060 \pm 0.008$A, and $\beta = 104.91 \pm 0.03°$. The density for four molecules per cell is 1.87g cm$^{-3}$. These data establish that the molecular structure of 3,7-dicyano-1,4-dithiino[2,3-c; 6,5-c']diisothiazole is trans as shown in I.

The dipotassium salt of bis(2-mercapto-1,2-dicyanovinyl)sulfide employed as a catalyst was prepared by the following procedure. Tetracyano-1,4-dithiin (10.8 g, 0.05 mole) in 200 ml of acetone was added over one-half hour to 16.0 g (0.1 mole) of potassium ethyl xanthate in 500 ml of acetone. After ½ hour of additional stirring, the solvents were removed in vacuo, and the residue was extracted several times with 50-ml portions of low-boiling petroleum ether under reflux. The insoluble residue (19 g) was dissolved in 300 ml of acetone, filtered and 1 l of chloroform was added to the filtrate. A total of 11 g (65%) of the dipotassium salt of bis(2-mercapto-1,2-dicyanovinyl)sulfide was obtained as a yellow solid which melted with decomposition at 280°-285° C. The infrared spectrum showed characteristic bands at 4.53 (C≡N) and 6.76 $\mu$(C=C) and the ultraviolet spectrum (EtOH) showed $\lambda_{max}$ 380 nm ($\epsilon$ 18,400) and 218 (16,950).

Anal. Calcd. for C$_8$N$_4$S$_3$K$_2$: C, 29.42; H, 0.00; N, 17.16; S, 29.46. Found: C, 28.70; H, 0.40; N, 17.31; S, 29.51.

EXAMPLE 2

3,7-Dicyano-1,4-dithiino[2,3-c; 6,5-c']diisothiazole (Formula I, R = -CN)

An improved yield of the dicyano product was obtained by the following procedure. 1,2-Dimethoxyethane (900 ml), sulfur (20.25 g, 0.633 eq) and sodium iodide (2.7 g, 18 meq) were heated under reflux for 5 minutes. The suspension was cooled to room temperature and tetracyano-1,4-dithiin (32.4 g, 0.15 eq) was added. The reaction mixture was heated under reflux (83°-84° C) for 20 hours, cooled, and a few crystals of 3,7-dicyano-1,4-dithiino[2,3-c; 6,5-c']diisothiazole authenticated according to the spectral and analytical procedures of Example 1 were added. The mixture was cooled (−78° C) with stirring for 1 hour and the crude product (43.7 g, ~100% yield) was separated by filtration. Recrystallization once from toluene (decolorizing carbon was used) gave pure 3,7-dicyano-1,4-dithiino[2,3-c; 6,5-c']diisothiazole.

EXAMPLES 3-5

In the following examples, use of the catalysts shown in Column II gave yields of 3,7-dicyano-1,4-dithiino-[2,3-c; 6,5-c']diisothiazole shown in Column III.

| Example | Catalyst | Yield, % |
|---|---|---|
| 3 | (C$_2$H$_5$)$_3$N | 59 |
| 4 | K$_2$S$_x$ | 52 |
| 5 | Diisopropylethylamine | (a) |

(a) Reaction was carried out for 2.25 hours, and a mixture of 3,7-dicyano-1,4-dithiino[2,3-c; 6,5-c']diisothiazole (40% yield) and product II of Example 6 was obtained.

EXAMPLE 6

1,4-Dithiino[2,3-c; 6,5-c']diisothiazole (Formula I, R = -H)

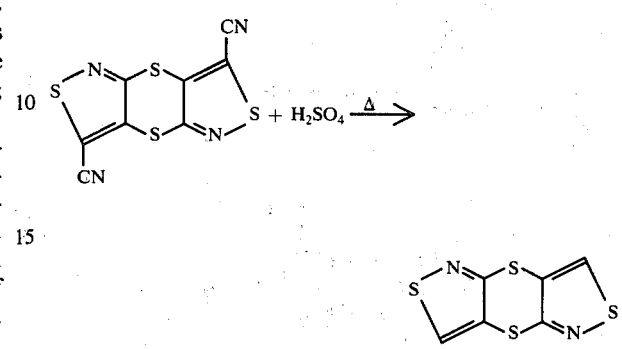

A mixture of 0.28 g (1 meq) of 3,7-dicyano-1,4-dithiino[2,3-c; 6,5-c']diisothiazole, 21 ml of concentrated sulfuric acid and 7 ml of water was heated at 170° C for 15 minutes. The yellow solution was cooled to room temperature and poured over ice. The suspension was filtered, and the solid was extracted with 1N sodium hydroxide solution to leave a residue of colorless, solid 1,4-dithiino[2,3-c; 6,5-c']diisothiazole.

EXAMPLE 7

1,4-Dithiino[2,3-c; 6,5-c']diisothiazole

Example 6 was repeated on a larger scale to obtain sufficient product for analysis and characterization. The reaction with sulfuric acid was carried out with 4.6 g of 3,7-dicyano-1,4-dithiino[2,3-c; 6,5-c']diisothiazole and was allowed to proceed at 180° C for 3 hours at which time the solution was colorless. The crude product isolated as in Example 6 was recrystallized from chlorobutane to give pure 1,4-dithiino[2,3-c; 6,5-c']diisothiazole, mp 190°-191° C.

Anal. Calcd. for C$_6$H$_2$N$_2$S$_4$: C, 31.3; H, 0.88; N, 12.2; S, 55.7; m.w. 230.34. Found: C, 32.1; H, 1.42; N, 12.2; S, 54.5.

Mass spectral analysis: m/e Calcd, 229.9101; Found, 229.9097.

NMR(DMSO-d$_6$): ($\delta$) 9.0–9.1 ppm (singlet).

UV: (CH$_3$CN): $\lambda_{max}$ 295 nm ($\epsilon$ 11,500), 211 (17,900)

IR(KBr): 3.73 and 3.26 (s, = CH), 6.10 and 6.80(w), (conjugated), cyclic C=C and/or C = N),7.59(s), 7.75(s), 11.85(w), 12.15(m), 12.35(w), 12.55(w), 12.78(w) $\mu$.

Use of 1,4-dithiino[2,3-c; 6,5-c']diisothiazole as a fluorescence brightener was demonstrated as follows. A sample of a multifabric swatch was immersed in an aqueous suspension of the diisothiazole, and the suspension was heated at 100° C for 30 minutes. The swatch was removed, rinsed well with distilled water and dried. The dried swatch was examined under an ultraviolet light using an untreated swatch as a control. All the fabrics of the swatch exhibited some fluorescence.

EXAMPLE 8

1,4-Dithiino[2,3-c; 6,5-c']diisothiazole-3,7-dicarboxylic Acid (Formula I, R = -CO₂H)

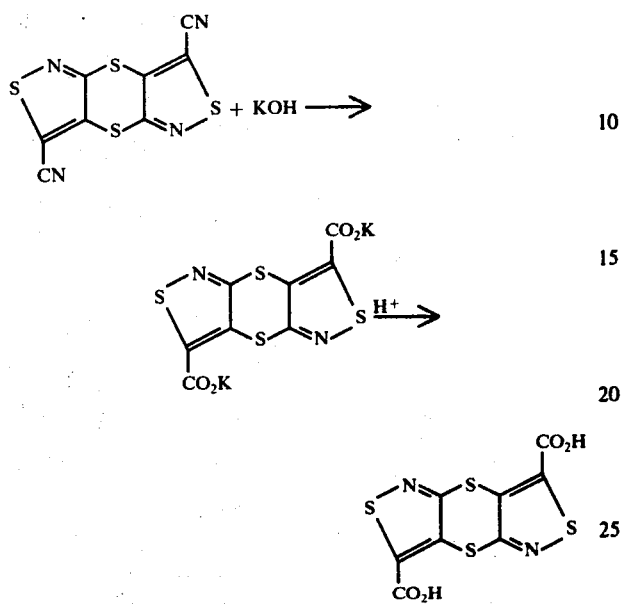

Potassium hydroxide (1.4 g, 25 meq) was dissolved in 25 ml of water and 1.0 g (3.6 meq) of 3,7-dicyano-1,4-dithiino[2,3-c; 6,5-c']diisothiazole was added. Nitrogen was bubbled through the suspension while it was heated slowly to reflux. A vigorous nitrogen purge was continued at reflux to assist in removal of ammonia. After 4-5 hours, the solid had dissolved completely. Upon cooling to room temperature, the dipotassium salt of 1,4-dithiino-[2,3-c; 6,5-c']diisothiazole-3,7-dicarboxylic acid separated from solution. The salt was separated by filtration, dissolved in water, and the solution was heated to 100° C and neutralized with 6N hydrochloric acid. Upon cooling, intensely yellow-colored crude 1,4-dithiino[2,3-c; 6,5-c']-diisothiazole-3,7-dicarboxylic acid was separated and isolated, mp 230°-247° C. The acid can be purified by crystallization from glacial acetic acid, and it can be further purified by suspension in hot water followed by filtration of the hot suspension. The purified product, mp 230° C (dec), fluoresced in the presence of ultraviolet light.

Anal. Calcd. for $C_8H_2O_4N_2S_4$: C, 30.2; H, 0.63; N, 8.80; S, 40.3. Found: C, 30.5; H, 1.01; N, 8.72.

UV (separate sample) EtOH): $\lambda_{max}$ 368 nm ($\epsilon$ 11,700), 277 (4900), 219 (29,500).

(0.1N NaOH): $\lambda_{max}$ 352 nm ($\epsilon$ 10,900), 273 (3980).

IR(KBr): 3.0-4.0 (broad, H bonded —OH), 5.95 (s, carbonyl) 6.66 (s, conjugated C=C and/or C=N), 7.09, 7.50, 8.03 (s, C-O), 10.29, 12.19, 14.05 μ.

Mass spectral analysis of a silylated sample of the product showed peaks at m/e 462 and 457 supporting the presence of two carboxyl groups.

EXAMPLE 9

1,4-Dithiino[2,3-c; 6,5-c']diisothiazole-3,7-dicarboxylic Acid (Formula I, R = -CO₂H)

3,7-Dicyano-1,4-dithiino[2,3-c; 6,5-c']diisothiazole (0.28 g) and 50 ml of concentrated hydrochloric acid were heated under reflux overnight. The resulting solution was cooled and poured over ice. The deep yellow solid dicarboxylic acid was separated by filtration and its identity confirmed by infrared analysis.

EXAMPLE 10

1,4-Dithiino[2,3-c; 6,5-c']diisothiazole-3,7-dicarbonyl Chloride (Formula I, R = -COCl)

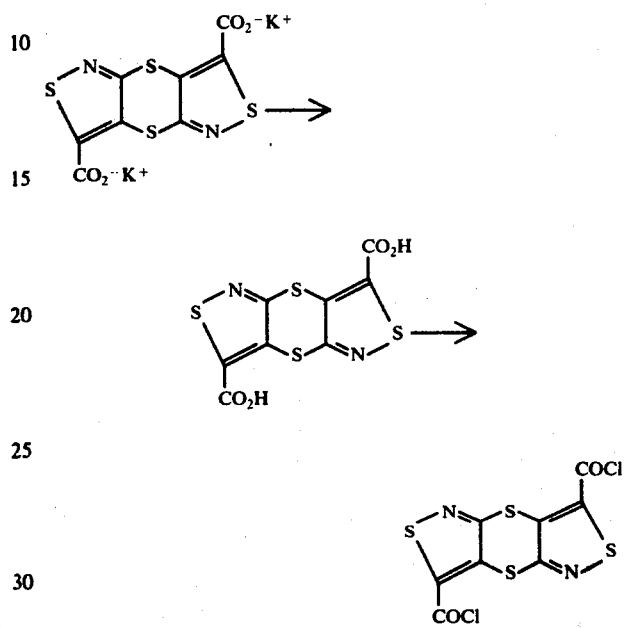

One gram (2.5 meq) of the dipotassium salt of 1,4-dithiino[2,3-c; 6,5-c']diisothiazole-3,7-dicarboxylic acid was acidified with 6N hydrochloric acid, and the suspension was stirred for one-half hour. The intermediate dicarboxylic acid was separated by filtration and mixed with 74 ml of thionyl chloride and 0.5 ml dimethylformamide. The reaction mixture was heated under reflux for 6 hours, cooled to room temperature, and 1,4-dithiino[2,3-c; 6,5-c']diisothiazole-3,7-dicarbonyl chloride was precipitated as an orange solid, mp 236°-237° C.

Additional analytical data were obtained on a similarly prepared sample of the dicarbonyl chloride.

Anal. Calcd. for $C_8N_2S_4O_2Cl_2$: C, 27.1; N, 7.89; S, 36.1; Cl, 20.0. Found: C, 27.1; N, 7.69; Cl, 19.9.

UV(CH₂Cl₂): $\lambda_{max}$ 411 nm ($\epsilon$ 10,900), 301 (9,380).

IR(KBr): 5.84 (s, carbonyl), 6.84 (s, conjugated C=C and/or C=N), 7.45(s), 7.55(s), 7.75(s), 7.85, 8.50, 10.13 (s), 10.54, 12.06(s), 14.2-14.3 (broad) μ.

EXAMPLE 11

N,N,N',N'-Tetramethyl-1,4-dithiino[2,3-c; 6,5-c']-diisothiazole-3,7-dicarboxamide (Formula I, R = -CON(CH₃)₂)

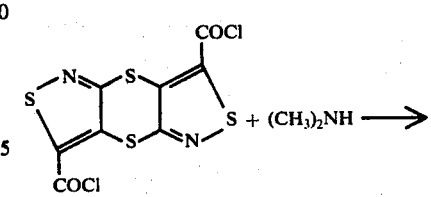

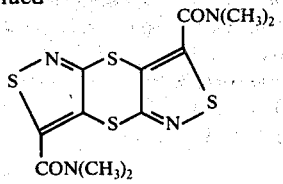

A mixture of 0.41 g of 1,4-dithiino[2,3-c; 6,5-c']diisothiazoledicarbonyl chloride and 80 ml of aqueous dimethylamine was stirred at room temperature for 30 minutes. The crude product was separated by filtration and recrystallized from chlorobutane to give N,N,N',N'-tetramethyl-1,4-dithiino[2,3-c; 6,5-c']diisothiazole-3,7-dicarboxamide as a pale yellow solid, mp 218°–220.5° C.

Anal. Calcd. for $C_{12}H_{12}N_4O_2S_4$: C, 38.7; H, 3.25; N, 15.0; S, 34.4. Found: C, 39.4; H, 3.08; N, 14.4; S, 34.4.

IR(KBr): 2.93 (b, sec. amide), 3.43, 6.16 (s, carbonyl), 6.71, 6.98, 7.20, 7.80(s), 7.94, 8.45, 9.14, 9.40, 10.34, 10.83, 11.40, 13.38, 14.99 μ.

UV(CH$_2$Cl$_2$): $\lambda_{max}$ 309 nm ($\epsilon$10,816).

A solution of the dicarboxamide in ether was fluorescent when irradiated with ultraviolet light. Use of the dicarboxamide as a fluorescence brightener was demonstrated as follows: A sample of a multifabric swatch was immersed in an aqueous suspension of the dicarboxamide, and the suspension was heated at 100° C for 30 minutes. The swatch was removed, rinsed well with distilled water and dried. The dried swatch was examined under an ultraviolet light using an untreated swatch as a control. All the fabrics of the swatch exhibited fluorescence.

When dimethylamine is replaced with the amines listed below, the corresponding dicarboxamides are obtained:

methylamine, ethylamine, n-propylamine, n-butylamine, n-pentylamine, i-propylamine, sec-butylamine, diethylamine, 2-pentylamine, N-methyl-1-propylamine, N-ethyl-1-propylamine, di-isopropylamine, N-methyl-1-butylamine, N-propyl-1-butylamine, 3-pentylamine, N-propyl-1-pentylamine, N-methyl-3-pentylamine and ammonia.

EXAMPLE 12

Dimethyl 1,4-dithiino[2,3-c; 6,5-c']diisothiazole-3,7-dicarboxylate (Formula I, R = CO$_2$CH$_3$)

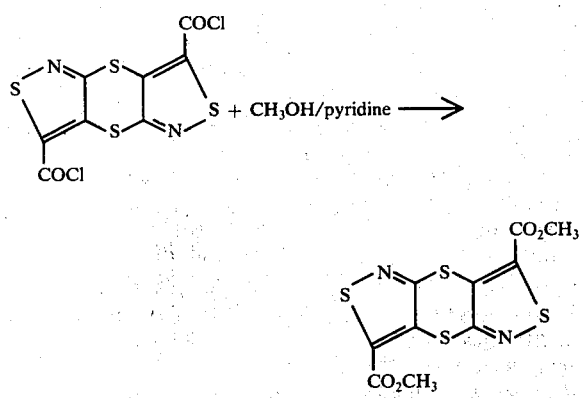

A total of 2 g (5.6 meq) of 1,4-dithiino-[2,3-c; 6,5-c']diisothiazole-3,7-dicarbonyl chloride was added with stirring at room temperature under nitrogen to a mixture of 25 ml of methanol and 25 ml of pyridine, and the suspension was stirred for an additional 2.5 hours. The crude solid product was separated, washed with water and dilute hydrochloric acid to give 2.13 g of crude ester. Two recrystallizations from chlorobutane gave pure dimethyl 1,4-dithiino[2,3-c; 6,5-c']diisothiazole-3,7-dicarboxylate, mp 240°–243° C.

Anal. Calcd. for $C_{10}H_6N_2S_4O_4$: C, 34.7; H, 1.75; N, 8.09; S, 37.0. Found: C, 35.0; H, 1.94; N, 8.04.

UV(CH$_2$Cl$_2$): $\lambda_{max}$ 372 nm ($\epsilon$ 12,110), 280 (6055).

When methanol is replaced with the alcohols listed below, the corresponding dicarboxylates are obtained:

1-propanol, 2-propanol, 1-butanol, sec-butanol, isobutyl alcohol, t-butyl alcohol, 1-pentanol 2-pentanol, 3-pentanol, 3-methyl-2-butanol and 3-methyl-3-butanol.

EXAMPLE 13

Diethyl 1,4-dithiino[2,3-c; 6,5-c']diisothiazole-3,7-dicarboxylate (Formula I, R = -CO$_2$C$_2$H$_5$)

When methanol is replaced by ethanol in the procedure of Example 12, there is obtained diethyl 1,4-dithiino[2,3-c; 6,5-c'diisothiazole-3,7-dicarboxylate with mp 191°–193° C.

EXAMPLE 14

Dibenzyl 1,4-dithiino[2,3-c; 6,5-c']diisothiazole-3,7-dicarboxylate (Formula I, R = -CO$_2$CH$_2$C$_6$H$_5$)

When methanol is replaced by benzyl alcohol in the procedure of Example 12, there is obtained dibenzyl 1,4-dithiino[2,3-c; 6,5-c']diisothiazole-3,7-dicarboxylate with mp 245° C.

EXAMPLE 15

N,N'-Bis(4-methoxyphenyl)-1,4-dithiino[2,3-c; 6,5-c']diisothiazole-3,7-dicarboxamide (Formula I, R = 4-CH$_3$OC$_6$H$_4$NHCO-)

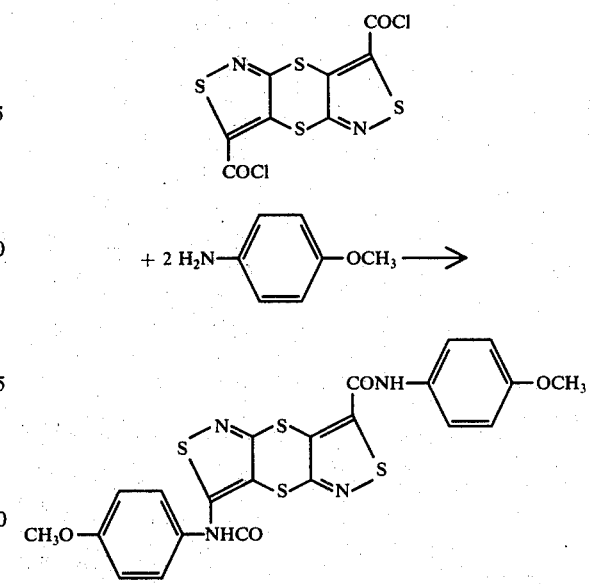

A mixture of 1,4-dithiino[2,3-c; 6,5-c']diisothiazole-3,7-dicarbonyl chloride (2.0 g, 5.6 mmole), 97% p-anisidine (3.0 g, 23.6 mmole) and 1,2-dichloroethane (60 ml) was stirred at reflux. More solvent was added during the reaction as a yellow solid precipitated. After 2 hr reflux, the mixture was cooled, filtered, and washed successively with 1,2-dichloroethane, water, 2B alcohol, and ether to give 2.895 g (5.48 mmole, 98%) of yellow solid product, mp ~330° C. Recrystallization of this product from N,N-dimethylformamide (DMF) (~70 ml) gave pure N,N'-bis(4-methoxyphenyl)1,4-dithiino[2,3-c; 6,5-c']diisothiazole-3,7-dicarboxamide with mp 336°–339° C.

Anal. Calcd. for $C_{22}H_{16}N_4S_4O_4$: C, 49.98; H, 3.05; N, 10.60; S, 24.26 Found: C, 50.09; H, 3.28; N, 10.64; S, 24.44 24.22.

When p-anisidine is replaced with the amines listed below, the corresponding dicarboxamides have the structures and names shown in Examples 16–20.

| | DICARBOXAMIDES DERIVED FROM AROMATIC AMINES | |
|---|---|---|
| Example | Amine | Formula I Product | mp of Product° C |
| 16 | p-Nitroaniline | R = 4-$O_2NC_6H_4$NHCO-N,N'-bis(4-nitrophenyl)-1,4-dithiino[2,3-c; 6,5-c']diisothiazole-3,7-dicarboxamide | >370° dec. |
| 17 | p-Toluidine | R = 4-$CH_3C_6H_4$NHCO-N,N'-bis(4-tolyl)-1,4-dithiino[2,3-c; 6,5-c']diisothiazole-3,7-dicarboxamide | 353–355° |
| 18 | o-Nitroaniline | R = 2-$O_2NC_6H_4$NHCO-N,N'-bis(2-nitrophenyl)-1,4-dithiino[2,3-c; 6,5-c']diisothiazole-3,7-dicarboxamide | 350–353° |
| 19 | N-Methyl-p-nitroaniline | R = 4-$O_2NC_6H_4$N-($CH_3$)CO-N,N'-bis(4-nitrophenyl)-N,N'-dimethyl-1,4-dithiino[2,3-c; 6,5-c']diisothiazole-3,7-dicarboxamide | >350° dec. |
| 20 | N-Methyl-o-nitroaniline | R = 2-$O_2NC_6H_4$N-($CH_3$)CO-N,N'-bis(2-nitrophenyl)-N,N'-dimethyl-1,4-dithiino[2,3-c; 6,5-c']diisothiazole-3,7-dicarboxamide | >350° dec. |

EXAMPLE 21

3,7-Dicyano-1,4-dithiino[2,3-c; 6,5-c']diisothiazole (formula I, R = -CN)

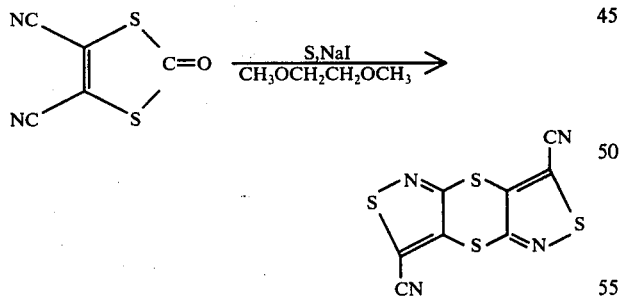

The reaction was run under nitrogen in a flask equipped with a reflux condenser and stirrer. 1,2-Dimethoxyethane (500 ml) was transferred under $N_2$ into the flask, and sulfur (60 g, 1.875 eq) and sodium iodide (20 g, dried over refluxing benzene) were added. The mixture was stirred at reflux (83°–84° C) for 0.5–1 hr, until a clear yellow solution had formed. The mixture was cooled to ~50° C, and treated with 4,5-dicyano-1,3-dithiolen-2-one (25 g, 0.149 mole, prepared by the method of C. G. Krespan, U.S. Pat. No. 3,140,295, and recrystallized from benzene). The mixture was stirred at reflux (83°–84° C) for 18 hr, then it was cooled to 0° C (wet ice/acetone), and filtered. The solid residue of product was washed with water and carbon disulfide to remove inorganic salts and sulfur, and dried. The yield was 11.06 g (0.039 mole, 53%), mp 280° C. There was no mixture mp depression with a sample of 3,7-dicyano-1,4-dithiino[2,3-c; 6,5-c']diisothiazole prepared by the method of Example 1.

EXAMPLE 22

Bis(tetrabutylammonium)-1,4-dithiino[2,3-c; 6,5-c']-diisothiazole-3,7-dicarboxylate (Formula I, R = -$CO_2^-$(n-$C_4H_9$)$_4$N+)

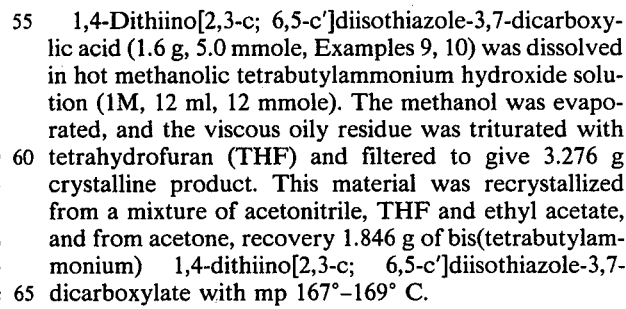

1,4-Dithiino[2,3-c; 6,5-c']diisothiazole-3,7-dicarboxylic acid (1.6 g, 5.0 mmole, Examples 9, 10) was dissolved in hot methanolic tetrabutylammonium hydroxide solution (1M, 12 ml, 12 mmole). The methanol was evaporated, and the viscous oily residue was triturated with tetrahydrofuran (THF) and filtered to give 3.276 g crystalline product. This material was recrystallized from a mixture of acetonitrile, THF and ethyl acetate, and from acetone, recovery 1.846 g of bis(tetrabutylammonium) 1,4-dithiino[2,3-c; 6,5-c']diisothiazole-3,7-dicarboxylate with mp 167°–169° C.

Anal. Calcd. for $C_{40}H_{72}N_4S_4O_4$: C, 59.95; H, 9.06; N, 6.99; S, 16.01 Found: C, 59.64; H, 8.92; N, 7.31; 59.89, 9.10, 7.41 S, 15.88 15.72.

UTILITY

The compounds of the invention are useful in a number of ways. The dinitrile serves as the key intermediate to the other compounds of the invention which have their own utilities. For example, the dipotassium salt of 1,4-dithiino[2,3-c; 6,5-c']diisothiazole-3,7-dicarboxylic acid is useful as a pH indicator.

EXAMPLE A

A series of buffer solutions of pH 1-10 were prepared. A piece of filter paper was heated under reflux for 0.5 hour in a suspension of the dipotassium salt of 1,4-dithiino[2,3-c; 6,5-c']diisothiazole-3,7-dicarboxylic acid (2.0 g) in 60-80 ml of water. The paper was dried, cut into strips, and the strips dipped into the various buffer solutions. The progressive change in color of the strips as the pH is raised, as shown in the following table, demonstrates that the salt is a useful indicator of acidity.

| pH | Color of Paper |
|---|---|
| 1 | Intense yellow |
| 2 | Yellow |
| 3 | Pale yellow |
| 4 | Very pale yellow; nearly colorless |
| 7 | Colorless |
| 10 | Colorless |

The dicarboxylic acid is a useful fluorescing agent and dye.

EXAMPLE B

An aqueous suspension of the dipotassium salt of 1,4-dithiino[2,3-c; 6,5-c']diisothiazole-3,7-dicarboxylic acid (2.0 g) in 60-80 ml of water was heated to reflux and a multifilament fabric swatch was added. Heating was continued for 1 hour, the fabric was removed, washed with cold water and dried. The cotton and viscose rayon sections of the swatch showed fluorescence in the presence of ultraviolet light.

The swatch was acidified in a dilute solution of acetic acid. All the fibers were dyed yellow, and the nylon, silk and acetate portions of the swatch fluoresced intensely in the presence of ultraviolet light.

The diacid chloride of the invention is particularly useful for the preparation of fluorescent polyamides. The diacid chloride and the dicarboxylates are useful components for the preparation of polyethers and polyester glycols, useful in polyester and polyurethane resin formulations.

EXAMPLE C

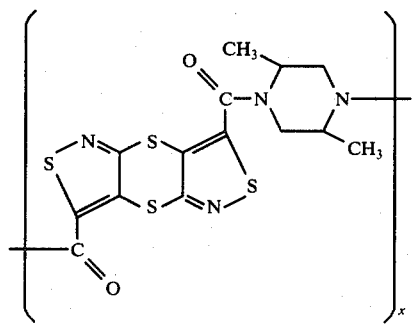

A suspension of 2.0 g (5.6 meq) of 1,4-dithiino[2,3-c; 6,5-c']diisothiazole-3,7-dicarbonyl chloride in 200 ml of dry methylene chloride was added rapidly to a jacketed blender, cooled with ice water, which contained 0.75 g (6.6 meq) of trans-2,5-dimethylpiperazine, 200 ml of water, 11.27 ml of 1N aqueous sodium hydroxide solution and 31 ml of methylene chloride. The suspension was stirred rapidly for 0.5 (pH = 10). The methylene chloride was removed at reduced pressure, and the crude polymer was separated by filtration, washed with acetone, water, and dried, yield 2.25 g of pale yellow polyamide.

The polyamide was fractionated with chloroform to give two fractions, chloroform insoluble (A), and chloroform soluble (B).

A. 1.27 g, pale yellow granular solid, dec 335°-360°C, inherent viscosity, $\eta_{inh}$ 0.88 (0.1% Conc $H_2SO_4$, 25°).

B. 0.42 g, bright yellow/orange solid, dec 318° C, $\eta_{inh}$ 0.07 (0.1% Conc $H_2SO_4$, 25°).

Both A and B fluoresced in the solid state in the presence of ultraviolet light, and films of both A and B (from methanesulfonic acid) also showed fluorescence.

Solution polymerization (dimethylacetamide) of 1,4-dithiino[2,3-c; 6,5-c']diisothiazole-3,7-dicarbonyl chloride with trans-2,5-dimethylpiperazine also gave a polyamide which fluoresced in the presence of ultraviolet light.

EXAMPLE D

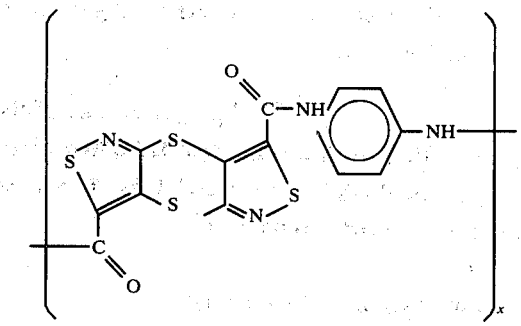

Solution polymerization of 1,4-dithiino[2,3-c; 6,5-c']diisothiazole-3,7-dicarbonyl chloride (2.0 g, 5.6 meq) with p-phenylenediamine (0.61 g, 5.6 meq) in 100 ml of hexamethylphosphoramide (HMPA) gave a polyamide which was fractionated to give HMPA insoluble (A) and HMPA soluble (B) fractions. Fraction B was precipitated by addition of water.

A. 0.33 g, dec 350° C, $\eta_{inh}$ 0.119 (0.1% Conc $H_2SO_4$, 25°).

B. dec 222° C.

Both A and B showed fluoresence in the solid state in the presence of ultraviolet light, and films of both A and B (from methanesulfonic acid) exhibited fluorescence.

EXAMPLE E

A dispersion (masstone) of 1,4-dithiino[2,3-c, 5,6-c'] diisothiazole-3,7-dicarboxylic acid (1g) and transparent varnish (1g) was prepared by mulling the mixture 10 times on a Hoover muller. A 1:30 extension of this dispersion was prepared by mixing, with a spatula, 0.175 g of the dispersion and 5g of a 3.2:1 zinc oxide-varnish paste. Both the masstone and extended dispersion were drawn to thin films in bond paper and used for the color and lightfastness determinations.

COLOR

The film colors are described by the Munsell indices ("Munsell Book of Color," Munsell Color Company, Inc., Baltimore, Maryland, 1966), 7.5Y 8.5/12 in masstone and 6Y 8.5/10 in 1:30 extension. In common terms, the color is a bright primrose yellow.

LIGHTFASTNESS

There was a barely perceptible change in masstone and extension films after 200 hours Fade-ometer® exposure (Type FDA-R Atlas Electric Devices Co., Chicago).

CHEMICAL RESISTANCE

Panels were prepared by milling the dry pigment with 30J alkyd vehicle to attain a pigment to binder ratio of 0.5. Panels were sprayed and baked at 250° F for 30 minutes.

A 30J alkyd panel was spotted with 4% aqueous solutions of hydrochloric acid, sulfuric acid, sodium hydroxide and sodium sulfide. The panel was heated to 140° F for 30 minutes. The panel exhibited good resistance to the four solutions.

BLEED

A TiO$_2$-30J alkyd strip was sprayed on one of the pigment panels. After heating to 250° F for 30 minutes, no evidence of bleed was observed.

I claim:

1. A diisothiazole of the formula

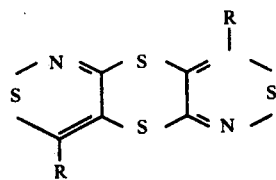

wherein both
R's are the same and are -H, -CN, -COCl, -CO$_2$R$^1$, -CONR$^2$R$^3$ or -CO$_2$-(alkyl)$_4$N$^+$,
R$^1$ is -H, alkyl of 1–5 carbon atoms, phenyl, -K or benzyl;
R$^2$ and R$^3$ are each selected from the group consisting of -H, alkyl of 1–5 carbon atoms, phenyl and phenyl substituted with alkyl, alkoxy, nitro, halo, or dialkylamino, in which the alkyl is from 1–5 carbon atoms.

2. The compound of claim 1, 3,7-dicyano-1,4-dithiino[2,3-c;6,5-c']diisothiazole.

3. The compound of claim 1, 1,4-dithiino[2,3-c; 6,5-c']diisothiazole.

4. The compound of claim 1, 1,4-dithiino[2,3-c; 6,5-c']diisothiazole-3,7-dicarboxylic acid.

5. The compound of claim 1, 1,4-dithiino[2,3-c; 6,5-c']diisothiazole-3,7-dicarbonyl chloride.

6. The compound of claim 1, N,N,N',N'-tetramethyl-1,4-dithiino[2,3-c;6,5-c']diisothiazole-3,7-dicarboxamide.

7. The compound of claim 1, dimethyl 1,4-dithiino-[2,3-c;6,5-c']diisothiazole-3,7-dicarboxylate.

8. The process of preparing the compound of claim 2 which comprises contacting and reacting tetracyano-1,4-dithiin or 4,5-dicyano-1,3-dithiolen-2-one with sulfur in 1,2-dimethoxyethane at a temperature of about 50°–280° C in the presence of a basic catalyst.

9. The process of claim 8 wherein the temperature is in the range of about 75°–85° C.

10. The process of claim 9 wherein the basic catalyst is an alkali metal iodide or a tertiary aliphatic amine.

* * * * *

UNITED STATES PATENT OFFICE
CERTIFICATE OF CORRECTION

PATENT NO. : 4,067,879

DATED : January 10, 1978

INVENTOR(S) : Susan Anne Vladuchick

It is certified that error appears in the above-identified patent and that said Letters Patent are hereby corrected as shown below:

Column 1, last line, "or" should be added at the beginning of the line.

Column 2, lines 23-37, the equation should read as follows:

(1)

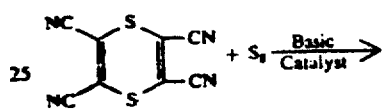

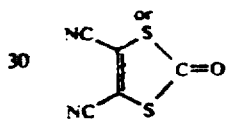

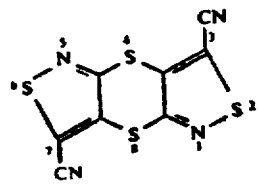

Column 4, line 45, "CH$_3$CH" should read --CH$_3$CN--.

Column 6, line 46, "C, 32.1; H, 1.42;" should read --C, $\overline{32.1}$; H, $\overline{1.42}$;--.

Column 6, line 49, "229,9101;" should read -- 229.9101; --.

UNITED STATES PATENT OFFICE
CERTIFICATE OF CORRECTION

PATENT NO. : 4,067,879

DATED : January 10, 1978

INVENTOR(S) : Susan Anne Vladuchick

It is certified that error appears in the above-identified patent and that said Letters Patent are hereby corrected as shown below:

Column 6, line 55, "(conjugated)," should read --(conjugated,--.

Column 8, line 47, "C, 27.1; N, 7.69; Cl, 19.9." should read --C, $\overline{27.1}$; N, $\overline{7.69}$; Cl,$\overline{19.9}$.--

Column 9, line 18, "C, 39.4; H, 3.08; N, 14.4; S, 34.4." should read --C, $\overline{39.4}$; H, $\overline{3.08}$; N, $\overline{14.4}$; S, $\overline{34.4}$.--

Column 10, line 24, "dithiino[2,3-c; 6,5-c'diisothiazole" should read --dithiino[2,3-c; 6,5-c']diisothiazole--.

Column 10, line 60, the "-NHCO" partial structure should read -- -NHCO --.

Column 12, line 67 and 68, should read -- 6.99; S, 16.01  Found: C, 59.64, 59.89; H, 8.92, 9.10; N, 7.31, 7.41; S, 15.88, 15.72. --

UNITED STATES PATENT OFFICE
CERTIFICATE OF CORRECTION

PATENT NO. : 4,067,879

DATED : January 10, 1978

INVENTOR(S) : Susan Anne Vladuchick

It is certified that error appears in the above-identified patent and that said Letters Patent are hereby corrected as shown below:

Column 14, line 6, "0.5 (pH = 10)" should read -- 0.5 hour (pH = 10) --.

Column 16, line 12, "$-CO_2-(alkyl)_4N+$" should read -- $CO_2^-(alkyl)_4N^+$ --.

Signed and Sealed this

Twenty-first Day of November 1978

[SEAL]

Attest:

RUTH C. MASON
Attesting Officer

DONALD W. BANNER
Commissioner of Patents and Trademarks